Figure 1:
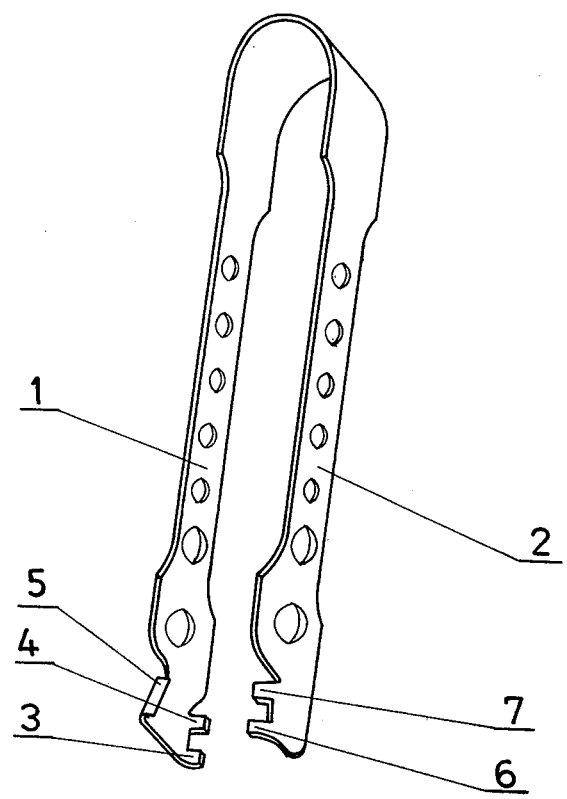

United States Patent [19]

Rucinski

[11] 4,244,094
[45] Jan. 13, 1981

[54] INSTRUMENT FOR REMOVING EXCHANGEABLE BLADES FROM SURGICAL SCALPES

[75] Inventor: Marek Ruciński, Nowy Tomysl, Poland

[73] Assignee: Fabryka Narzedzi Chirurgicznych, Nowy Tomyśl, Poland

[21] Appl. No.: 88,277

[22] Filed: Oct. 25, 1979

[30] Foreign Application Priority Data

Nov. 28, 1978 [PL] Poland .................................. 211289

[51] Int. Cl.³ ............................................ B25B 27/14
[52] U.S. Cl. ...................................... 29/270; 81/3 R; 294/16
[58] Field of Search ...................... 294/16; 30/1, 40.2, 30/339, 338, 342; 29/270, 278; 81/3 R

[56] References Cited

U.S. PATENT DOCUMENTS

| 3,172,316 | 3/1965 | Grieshaber | 30/339 |
| 3,374,025 | 3/1968 | Mantelet | 294/16 |
| 4,121,329 | 10/1978 | Sugiyama | 29/270 |

FOREIGN PATENT DOCUMENTS 1423345 2/1976 United Kingdom .

Primary Examiner—James B. Marbert
Attorney, Agent, or Firm—Ladas & Parry

[57] ABSTRACT

The instrument for removing exchangeable blades from surgical scalpes consists of two arms /1 and 2/ connected with each other and forming approximately the shape of the letter "U" or "V". The end of the arm /1/ is provided with two protrusions /3 and 4/ and with the catch disposed at a distance therefrom /5/, the end of the arm /2/ being provided with two similar protrusions /6 and 7/. The protrusions /3 and 4, and 6 and 7/ of both arms /1 and 2/ are displaced against each other by such a distance that under the influence of the arms /1 and 2/ by means of the protrusions /3, 4, 6, 7/ onto the blade /11/ mounted on the scalped /10/ it follows a bending of the dull-edged end of the blade /11/ above the upper plane of the lock /9/ of the scalpel /10/, and catching against the catch /5/. The blade /11/ bent in this way acts onto the instrument with a tangential force and gets put out from the lock /9/ of the scalpel /10/.

1 Claim, 3 Drawing Figures

INSTRUMENT FOR REMOVING EXCHANGEABLE BLADES FROM SURGICAL SCALPES

This invention relates to an instrument for removing exchangeable blades from surgical scalpels.

Instruments known from the British Pat. No. 1,423,345, published on Feb. 4, 1976, show a construction approximating to that of scissors the tips of arms whereof are provided with a grip for removing the blades. The closed grip shows in its section a rectangular opening having the dimensions matched to the dimensions of the scalpel lock. The contact surfaces of two halves of the grip, constituting the working surfaces adhering to the surface of the blade shows such a curvature that under the influence of a pressure onto the blade the end of the blade gets deflected above the plane of the scalpel lock.

The object of the invention is to provide an instrument having a considerably simplier structure, and operating on quite different principle.

The instrument according to the invention is featured therewith that it composes of two arms connected with each other and forming approximately the shape of the letter "U" or "V", whereby the end of one arm is from the inner side provided with two protrusions having the height larger than the height of the upper part of the scalpel lock and a spacing larger than the width of the lock, and with a catch disposed at a distance from the protrusions having the length equal to or larger than the thickness of the blade, being inclined to the longitudinal axis of the arms under an acute angle approximately equal to the inclination angle of the bevel of the scalpel lock, and the end of the other arm is from its inner side provided with two similar protrusions having the length larger than the whole length of the lock and with the spacing larger than the width of the length, and moreover the protrusions of the arms are displaced in relation to each other by such a distance that under the action of the pressure of the arms onto the blade mounted on the scalpel the dull-edged end of the blade gets bent above the upper plane of the scalpel lock.

In the instrument constructed in this way the bending of the dull-edged end of the blade is performed by means of protrusions, and putting-out of the blade from the lock is performed by means of the catch.

Figure 2:
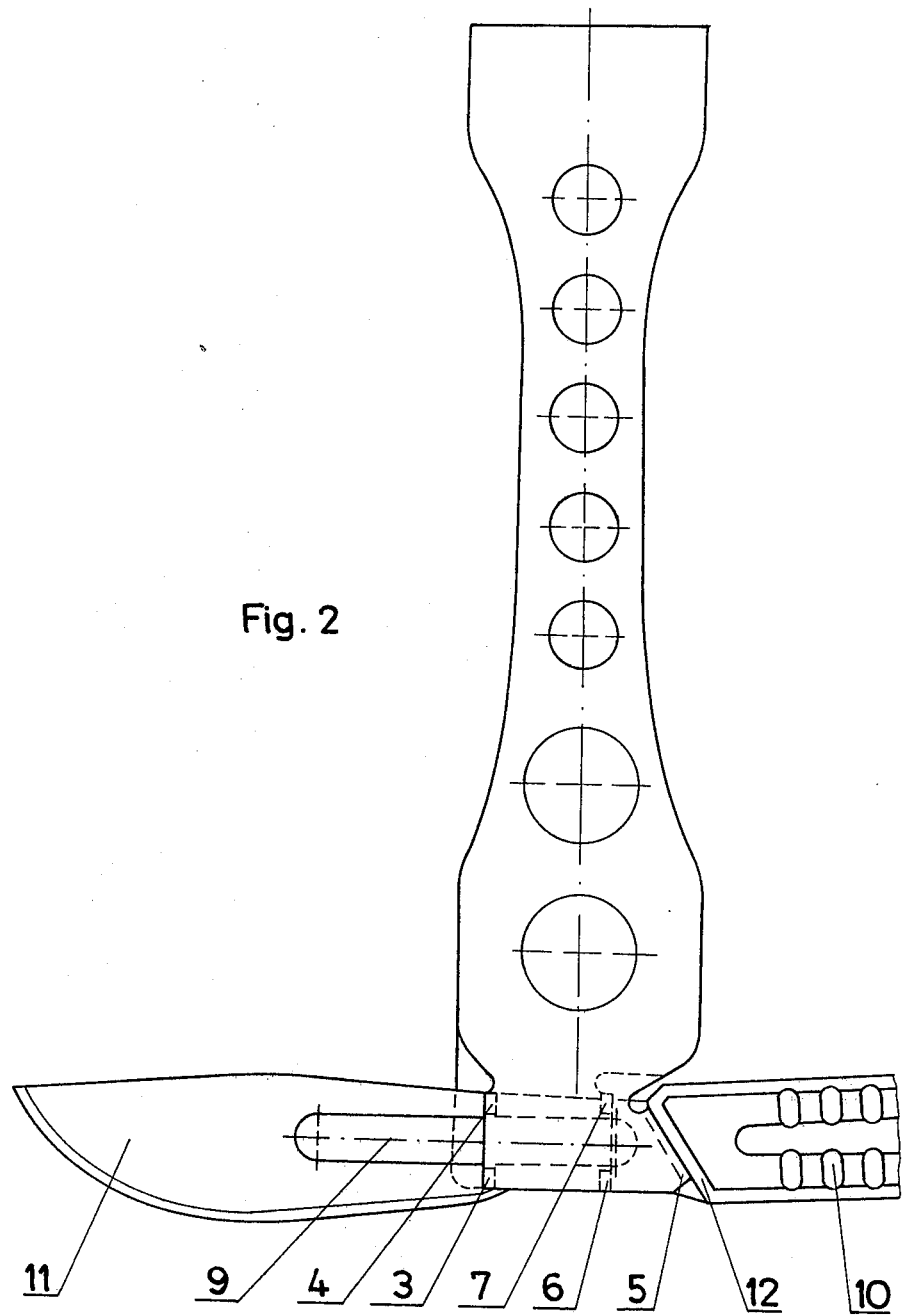
Figure 3:
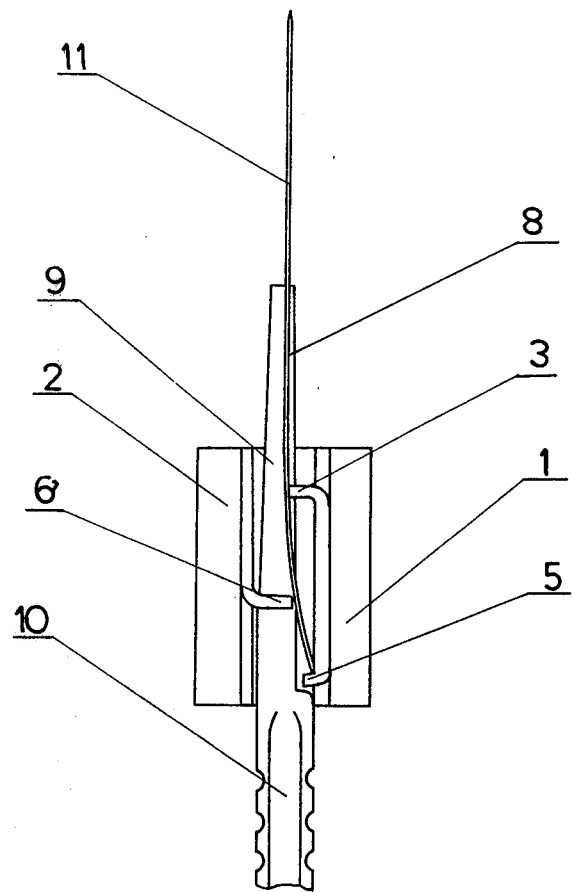

The invention will be now explained by means of an exemplary embodiment, with reference to the accompanying drawing, wherein FIG. 1 is an econometric projection of the instrument according to the invention;

FIG. 2 is the top view of the instrument and the scalpel in the position of removing the blade; and FIG. 3 is the front view of the instrument and the scalpel in the position of removing the blade.

The instrument according to the invention has two arms: the upper arm 1 and the lower arm 2, connected with each other, and formin approximately the form of the letter "U". At the end of the upper arm 1, at edges thereof, two protrusions 3 and 4 and the catch 5 are disposed, and at the end of the lower arm 2 two protrusion 6 an 7. The elements 3, 4, 5, 6, 7 are made of the same material as the arms 1 and 2.

The protrusions 3 and 4 have the height larger than the typical height of the upper part 8 of the lock 9 of the scalpel 10, and the spacing larger than the typical width of the lock 9. The catch 5 has the height equal to or larger than the thickness of the blade 11 of the scalpel 10 and is inclined to the longitudinal axis of the arms 1 and 2 under an acute angle, approximately equal to the angle of inclination of the bevel 12 of the lock 9 of the scalpel 10. The height of the protrusions 6 and 7 is however larger than the whole height of the lock 9, and the spacing—from the width of the lock 9.

The instrument constructed in this way is placed onto the lock 9 of the scalpel 10 (FIGS. 2 and 3) and under pressing with hand onto the arms 1 and 2 the protrusions 3 and 4 press onto the blade 11 of the scalpel 10 from above, and the protrusions 6 and 7 from below in result whereof the dull-edged end of the blade 11 is bent and comes under the catch 5. Then using a force tangential to the longitudinal axis of the scalpel 10 its blade 11 is put out from the grooves of the lock 9, not shown in the drawing.

The described exemplary embodiment of the invention does not excerpt all the constructional possibilities resulting from the scope of the patent claim. Another form of the instrument according to the invention can be a design consisting in connection of the arms 1 and 2 in the shape of the letter "V".

What is claimed is:

1. Instrument for removing exchangeable blades from surgical scalpels, characterized by that it consists of two arms connected with each other and forming approximately the shape of the letter "U" or "V", whereby the end of one arm is from the inner side provided with two protrusions having the height larger than that of the upper part of the lock of the scalpel, and the spacing larger than the width of the lock, and with a catch disposed at a distance from the protrusions, having the height equal to or larger than the thickness of the blade, inclined to the longitudinal axis of the arms under an acute angle approximately equal to the inclination angle of the bevel of the lock of the scalpel, and the end of the other arm is from the inner side provided with two similar protrusions having the height larger than the whole height of the lock of the scalpel and the spacing larger than the width of the lock of the scalpel, and moreover the protrusions of the arms are displaced against each other by such a distance that under the influence of pressure of the arms onto the blade mounted on the scalpel it follows a bending of the dull-edged end of the blade above the upper plane of the lock of the scalpel and catching on the catch.

* * * * *